US011134996B2

(12) United States Patent
Martin

(10) Patent No.: US 11,134,996 B2
(45) Date of Patent: Oct. 5, 2021

(54) LOW PROFILE DORSAL PLATE

(71) Applicant: ARTHREX, INC., Naples, FL (US)

(72) Inventor: Christopher Harris Martin, Salt Lake City, UT (US)

(73) Assignee: ARTHREX, INC., Naples, FL (US)

( * ) Notice: Subject to any disclaimer, the term of this patent is extended or adjusted under 35 U.S.C. 154(b) by 314 days.

(21) Appl. No.: 16/427,714

(22) Filed: May 31, 2019

(65) Prior Publication Data
US 2019/0314070 A1 Oct. 17, 2019

Related U.S. Application Data

(62) Division of application No. 13/023,228, filed on Feb. 8, 2011, now abandoned.

(51) Int. Cl.
*A61B 17/80* (2006.01)
*A61B 17/88* (2006.01)

(52) U.S. Cl.
CPC ...... *A61B 17/8061* (2013.01); *A61B 17/8085* (2013.01)

(58) Field of Classification Search
CPC ............ A61B 17/8061; A61B 17/8085; A61B 17/808; A61B 17/80; A61B 17/1686; A61B 17/1782; A61B 17/7291
USPC ..................... 606/70–71, 280–299
See application file for complete search history.

(56) References Cited

U.S. PATENT DOCUMENTS

| | | | |
|---|---|---|---|
| 5,718,705 A | 2/1998 | Sammarco | |
| 5,743,918 A * | 4/1998 | Calandruccio | A61B 17/1615 128/898 |
| 6,221,073 B1 * | 4/2001 | Weiss | A61B 17/8061 606/281 |
| 6,508,819 B1 | 1/2003 | Orbay | |
| 6,712,820 B2 | 3/2004 | Orbay | |
| 6,866,665 B2 | 3/2005 | Orbay | |
| 7,090,676 B2 | 8/2006 | Huebner et al. | |
| 7,137,987 B2 | 11/2006 | Patterson et al. | |
| 7,250,053 B2 | 7/2007 | Orbay | |
| 9,861,409 B1 * | 1/2018 | Agee | A61B 17/8872 |
| 2005/0273104 A1 | 12/2005 | Oepen et al. | |
| 2005/0288790 A1 * | 12/2005 | Swords | A61B 17/8085 623/17.19 |
| 2006/0025772 A1 * | 2/2006 | Leibel | A61B 17/1686 606/915 |
| 2006/0025796 A1 * | 2/2006 | Merced-O'Neill | A61B 17/32 606/190 |
| 2006/0173459 A1 | 8/2006 | Kay et al. | |
| 2010/0069966 A1 | 3/2010 | Castaneda et al. | |

* cited by examiner

*Primary Examiner* — Jessica Weiss
(74) *Attorney, Agent, or Firm* — Carlson, Gaskey & Olds

(57) ABSTRACT

A low profile dorsal plate for internal fixation of a radius fracture can comprise a single longitudinal portion having a distal end, and a transverse portion fixed across the distal end at an angle of about 15° to about 30° from perpendicular with respect to the longitudinal portion. The transverse portion can also have a z-axis curvature, or can be flexible to form a z-axis curvature, where the z-axis curvature corresponds to a dorsal contour of a distal radius. Also included is a first plurality of screw holes aligned within the longitudinal portion and a second plurality of screw holes aligned within the transverse portion.

19 Claims, 3 Drawing Sheets

LOW PROFILE DORSAL PLATE

CROSS-REFERENCE TO RELATED APPLICATION

This is a divisional of U.S. patent application Ser. No. 13/023,228, which was filed on Feb. 8, 2011.

BACKGROUND

Distal radius fractures are a common type of bone fracture of the radius of the forearm. The treatment of fractures of the distal radius has involved surgical and non-surgical means, such as casting. In the case of fractures involving many fragments of bone, treatment becomes progressively more difficult and casting, or non-surgical treatment, is generally less satisfactory. This is especially true when the articular surface, or joint surface, is fractured into multiple fragments. Such fractures, involving numerous fragments, are generally longitudinally unstable and have been treated with various devices to regain longitudinal stability. External fixation has provided longitudinal stability, but does not offer fixation means for multiple articular fragments. Furthermore, external fixation increases the risk of infection, since the pins screwed into the bone communicate with the outside and are thus contaminated. External fixation also frequently results in considerable wrist stiffness due to traction effects on the ligaments of the wrist.

Internal plate fixation with locking screws, in which the screws may be secured to the plate, offer an internal means of achieving longitudinal stability, thereby avoiding infection risks compared with external fixation. Internal plate fixation also allows for manipulation of multiple articular fragments and offers the potential to secure and longitudinally stabilize these fragments while not crossing the wrist joint itself, thereby facilitating rehabilitation and potentially minimizing the risks of wrist stiffness.

DETAILED DESCRIPTION

Reference will now be made to the examples illustrated, and specific language will be used herein to describe the same. Features and advantages of the technology will be apparent from the detailed description which follows, taken in conjunction with the accompanying drawings, which together illustrate, by way of example, features of the technology.

It is to be noted that, as used in this specification and the appended claims, the singular forms "a," "an," and "the" include plural referents unless the context clearly dictates otherwise.

Coordinate axes (e.g. "x", "y", and "z") are used herein to describe dimensional aspects of devices. For example, where longitudinal and transverse aspects of a device lie in a plane defined by x and y axes (i.e. the x-y plane), aspects that are perpendicular to this plane are considered to lie along the z-axis. Anatomical terms (e.g. "dorsal", "volar", "proximal", "distal") are used to describe axes, planes, directions relative to the body of a subject.

Figure 1A:
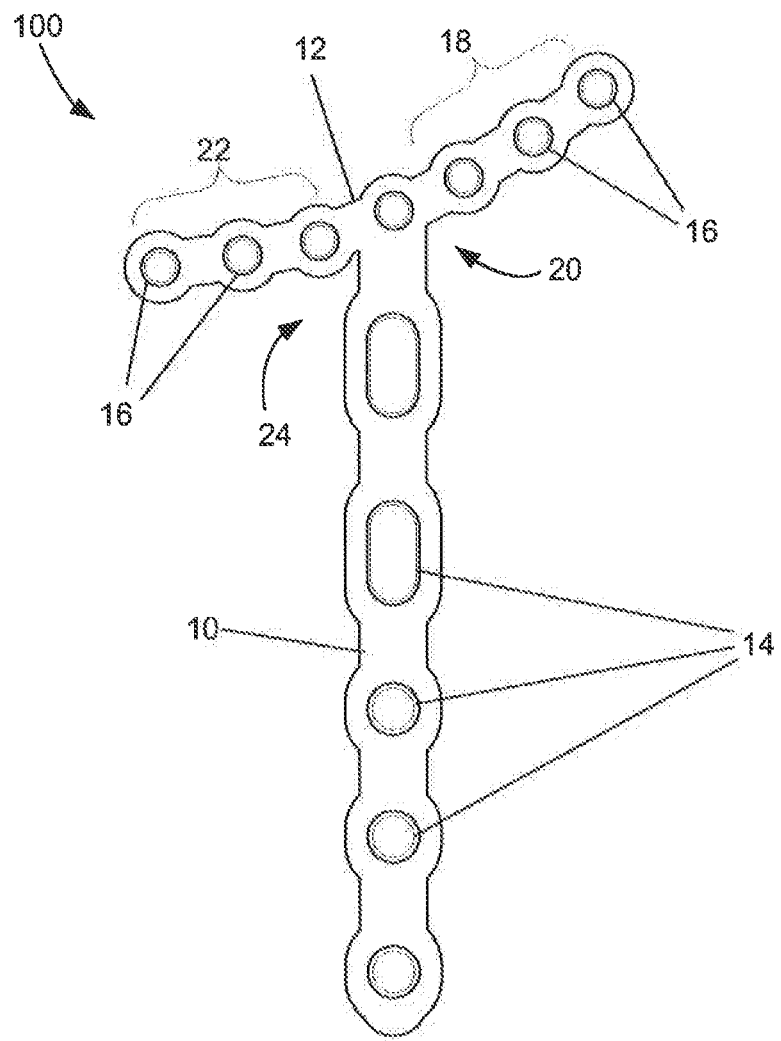
FIG. 1A is a top view diagram of a dorsal plate according to an example of the present disclosure.
Figure 1B:
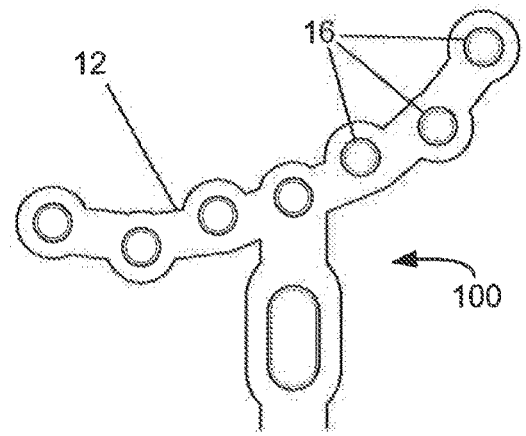
FIG. 1B is a top view diagram of the transverse portion of a dorsal plate according to another example of the present disclosure.

When referring to a "curve" or a "curvature," the context of that discussion will dictate which curvature is being discussed. For example, in some embodiments herein, the transverse portion will be described with respect to a curvature in an x-y plane (x-y curvature). Examples of this type of curvature are shown in FIGS. 1A and 1B. However, the transverse portion can also be curved, or be flexible or malleable enough for a surgeon to form a z-axis curvature (i.e. in a plane essentially perpendicular to the x-y axis) that corresponds to a dorsal contour of a distal radius.

When referring to a relative "angle" from perpendicular as it relates to the transverse portion fixed across the distal end of the longitudinal portion, the angle is measured from 90° where the transverse portion crosses the longitudinal portion. If the transverse portion is curved as shown in FIGS. 1A and 1B, then the tangent of the curve at the point of intersection is what is used to determine the angle from perpendicular.

Use of the term "flexibility" to describe portions of the dorsal plate herein means that the portion is manually bendable at room temperature by a human operator without requiring the assistance of powered tools.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the description herein.

As used herein, the term "substantially" refers to the complete or nearly complete extent or degree of an action, characteristic, property, state, structure, item, or result. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

Sizes, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 cm" should be interpreted to include not only the explicitly recited values of about 0.01 cm to about 2.0 cm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. This same principle applies to ranges reciting only one numerical value. Furthermore, such an interpretation should apply regardless of the breadth of the range or the characteristics being described.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

The present disclosure is directed to devices and methods for fixation of distal radial fractures. As used herein, the term "subject" refers particularly to a primate (e.g. a human), as well as to vertebrates having a wrist with skeletal structure and associated musculature in an arrangement similar to that seen in the wrist of primates.

Internal plate fixation can be accomplished with a plate designed for either the volar surface or the dorsal surface of the distal radius. The majority of fractures of the distal radius requiring operative treatment involve significant dorsal fragmentation and shortening of the bone. A dorsal surgical approach to the distal radius thereby affords direct access to the area of most damage to the bone in the majority of cases. A dorsal surgical approach also affords direct access to the articular or joint surface of the distal radius.

Prior dorsal plate designs, however, resulted in frequent complications, especially due to irritation and rupture of the extensor tendons at the wrist. As these complications became evident in clinical experience, practice shifted to fixation of dorsally displaced fractures using plates applied to the volar surface of the distal radius, allegedly avoiding the complications pertaining to the extensor tendons. The use of dorsal plates became less common.

However, certain difficulties are attendant on the use of volar plates. For example, access to the distal radius articular surface can be considerably more difficult to achieve from a volar surgical approach, due in part to the presence of the critical wrist (or radiocarpal) ligaments being present on the volar side of the wrist. Furthermore, due to the presence of dorsal damage, proper fixation involves driving fixing screws sufficiently far through the radius to engage the dorsal region, often penetrating the dorsal surface. Consequently, there have continued to be difficulties with extensor tendons caused by screws penetrating the dorsal aspect the distal radius and rubbing tendons directly. Furthermore, volar plates have typically been designed to be substantial enough to counteract the large bending moments on these plates (these bending forces are very minimal on dorsal plates), and therefore these plates are relatively thick. The thickness of these plates has resulted in attritional ruptures of the flexor tendons (especially to the thumb) due to friction of the flexor tendon on the plate.

Perhaps the most common difficulty is in obtaining congruence of the articular or joint surface of the distal radius due to limitations of the volar surgical approach, in which the volar ligaments should not be violated and direct visualization of the joint is therefore very difficult. Due to this difficulty with the volar surgical approach, surgeons have utilized greatly extended approaches to inspect the joint surface through the dorsal side of the wrist, or simply made a second exposure through the dorsal side of the wrist. To avoid further surgical dissection and morbidity, indirect visualization of the articular surface with fluoroscopic x-ray machines has been utilized. However, there are significant limitations in the resolution and accuracy of these machines in determining the congruence of the articular surface of the distal radius. In fact, there have been difficulties with screws placed from the volar side into the wrist joint due to an inability to see directly into the joint.

The present technology includes devices, systems, and methods for direct dorsal fixation that address some of the negative issues found with prior approaches. In accordance with this, a low profile dorsal plate for internal fixation of a radius fracture can comprise a single longitudinal portion having a distal end, and a transverse portion fixed across the distal end at an angle of about 15° to about 30° from perpendicular with respect to the longitudinal portion. The transverse portion can be linear in the x-y plane or have a curvature in the x-y plane. The transverse portion can also have a z-axis curvature that corresponds to a dorsal contour of a distal radius, or the transverse portion can be flexible to form such a curvature. Also included is a first plurality of screw holes aligned within the longitudinal portion and a second plurality of screw holes aligned within the transverse portion. In one specific embodiment, a system for dorsal fixation of a radius fracture can comprise the low profile dorsal plate described above, and a screw configured for insertion into bone and dimensioned to fit in at least one of the screw holes.

In another embodiment, a method for fixation of a distal radial fracture can comprise steps of partially dissecting a retinaculum of a wrist exhibiting a fractured distal radius to create a flap, and retracting tendons and the flap overlying the fractured distal radius. Once retracted, additional steps include attaching the dorsal plate described above to a distal extremity of the fractured distal radius, and securing the flap to cover the transverse portion. Thus, the transverse portion is covered by the retinaculum so that there is substantially no direct contact between the tendons and the transverse portion.

The wrist at the distal radius includes a large number of tendons connecting the extensor muscles to their points of insertion in the hand. These tendons are enclosed in a number of compartments formed by synovial sheaths and overlain by the fibrous dorsal carpal ligament, or retinaculum. Prior dorsal fixation devices often interfered with tendon function in this space, resulting in tendon rupture and other complications. The low profile plate of the present disclosure is shaped and dimensioned so as to minimize the space occupied by the plate among the various extensor compartments in the wrist. In particular, "low profile" as described herein refers to a relatively thin and narrow cross-section of the portions of the plate, such that the plate can reside among the wrist extensors without causing significant displacement of or friction against any extensors.

In another aspect, the transverse portion is sufficiently narrow and thin to cause minimal displacement or friction with respect to overlying wrist extensors, for example by being able to be covered by a flap of the retinaculum. Where the transverse portion and any attaching screws are covered by the retinaculum, these elements are thereby prevented from rubbing against overlying tendons. Therefore, complications otherwise associated with dorsal fixation approaches (i.e. irritation and rupture) can be avoided. This approach is facilitated by use of a dorsal plate with a narrow transverse portion, such that a relatively narrow section of the retinaculum is sufficient for use in covering the transverse portion. In a specific example, a strip of retinaculum having a width of around 1 cm can be sufficient to cover the transverse portion of the dorsal plate, though larger widths can also be used.

In each of these embodiments, the dorsal plate can be constructed of any material that is biocompatible and provides sufficient strength for fixing fragments in bone. In particular, metals are suitable for manufacture of dorsal plates, including iron, titanium, chromium, cobalt, molybdenum, and nickel, to name a few. In some embodiments, biocompatible alloys of these metals can be particularly suited for this use, such as stainless steel, cobalt chromium, and alloyed titanium.

Turning now to the FIGS., FIG. 1A shows a low profile dorsal plate 100 in accordance with an example of the present disclosure. The plate comprises a single longitudinal portion 10 configured for attachment along the longitudinal axis of the distal radius. In particular, the single longitudinal portion provides a sufficiently narrow longitudinal profile so that once attached to the bone, the longitudinal portion sits readily between adjacent extensor tendon compartments. In a particular aspect, the longitudinal portion is sufficiently narrow so as to fit between the tendons of two wrist extensors or between two tendon compartments when the plate is attached to the distal extremity of the radius of a subject. In a specific example, the longitudinal portion of the plate in accordance with the present disclosure can fit between the extensor pollicis longus (EPL) and the extensor carpus radialis brevis (ECRB) of the subject. In another aspect, the narrow profile of the single longitudinal portion allows for this component to have a thickness that provides sufficient resistance to bending forces that occur in the wrist, while still occupying a small cross-sectional space within the wrist. In an example, the longitudinal portion has a maximum width of less than about 1.25 cm.

Figure 2A:
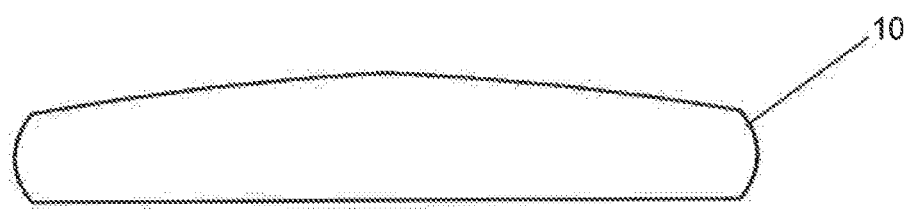
FIG. 2A is a cross-sectional diagram of the longitudinal portion of a dorsal plate according to an example of the present disclosure.
Figure 2B:
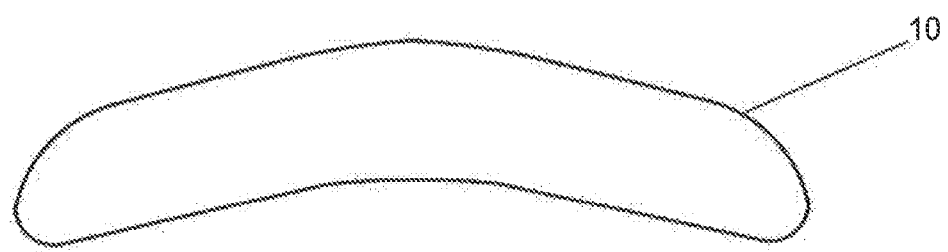
FIG. 2B is a cross-section diagram of the longitudinal portion of a dorsal plate according to another example of the present disclosure.

The longitudinal portion 10 can be configured for secure attachment to the radius. In one example as shown in FIG. 2A, the longitudinal portion can have a substantially flat cross-sectional profile. The narrow width of the longitudinal portion relative to that of the dorsal surface of the radius can allow secure and stable attachment of the plate with a flat profile. Alternatively, the longitudinal portion can exhibit a curved cross-section as shown in FIG. 2B, where the curvature can be substantially matched to a curvature of the radial surface for added stability. It is noted that FIGS. 2A and 2B are not necessarily drawn to scale.

Referring again to FIG. 1A, the dorsal plate 100 can further comprise a transverse portion 12 configured for attaching the plate to the distal extremity of the radius for purposes of fixing and stabilizing fractures. The transverse portion has dimensions that contribute to the low profile of the plate. In a particular example, the transverse portion has a maximum width of less than about 1 cm. In another aspect, the transverse portion is fixed at an angle across the distal end of the longitudinal portion 10. The angle between the transverse portion and longitudinal portion can be selected to correspond to the shape of the distal extremity of the radius. In particular, due to the styloid process of the distal radius, the dorsal aspect of the articular surface typically exhibits an angle so that the radial aspect of the surface extends farther distal than the ulnar aspect. The angle between the transverse portion and longitudinal portion of the plate can correspond to the angle of the articular surface. Specifically, the transverse portion can be situated so that the angle is from about 15° to about 30° from perpendicular to the longitudinal portion. In a more specific example, the angle is from about 18° to about 26°. In a still more specific example, this angle can be about 22°.

Depending on the size of the subject's radius or other factors (e.g. deformity or damage) affecting the shape of the bone, effective fixation may involve adjusting the angle between the transverse portion and the longitudinal portion. In one example, the distal end of the longitudinal portion can be configured at the junction with the transverse portion for adjustment of the angle. By way of non-limiting example, this feature can be provided by selecting a sufficiently flexible material for use at this location, or by giving the end a dimension that provides sufficient flexibility. Alternatively, the end can be configured to provide multiple selectable angles of connection to the transverse portion.

The dorsal plate as described herein can be attached to the radius using any type of fastener that can be applied through a dorsal surgical exposure, and that provides secure and stable attachment to bone. Fasteners known in the art for bone fixation include pins, wire, and screws. In a particular example, a system for dorsal fixation of a radius fracture can comprise a low profile dorsal plate as described herein together with at least one screw. Non-limiting examples of suitable screws include self-tapping screws, self-locking screws, cannulated screws, cortical bone screws, cancellous bone screws, and screws having combinations of features exhibited by these. Accordingly, to accommodate insertion of screws, the dorsal plate can include a plurality of screw holes. In a particular aspect, a plurality of screw holes can be distributed along the length of a component of the plate. More specifically as shown in FIG. 1A, the longitudinal portion can include a first plurality of screw holes 14, and the transverse portion can include a second plurality of screw holes 16.

The screw holes can be distributed and configured in such a way that is consistent with the low profile of the plate. In one aspect, a dorsal plate can include screw holes that are shaped to accept a screw to a depth so that the screw does not significantly increase the profile of the installed plate in the wrist. In a specific example, such a screw hole can include a countersink configuration. In another aspect, the plurality of screw holes can be distributed so as to occupy a minimal width. More specifically, the screw holes can be aligned within the shape of the longitudinal portion and the transverse portion. As used herein, the term "aligned" refers to an arrangement in which the centers of the holes are intersected by a single uninflected line or curve. Therefore, screw holes that are said to be "aligned" can be arranged in a single straight or curved line. This is illustrated in the plate of FIG. 1A, which includes a straight linear arrangement of the first plurality of screw holes 14 in the longitudinal portion, and a curved arrangement of the second plurality of screw holes 16. In an alternative example as shown in FIG. 1B, one or more of the screw holes may not be aligned, but rather, can deviate from this arrangement. For example, displacement of one or more screw holes can aid in placing screws in denser bone, or in order to place screws a sufficient distance from the line of a fracture.

The diameter of the screw holes can be selected to accommodate available types of bone screws. In a particular example, the average width of a component of the dorsal plate can be decreased by further narrowing the component width between two screw holes. In an alternative example, the component can have substantially the same width along its length. In such an example, the width can be selected to accommodate screw holes of a selected maximum diameter.

Screw holes included in the plate can include other features to aid in secure placement. In one example, a screw hole can include one or more features for securing the screw in place once inserted, such as threading to capture a threaded screw head. In another example, a screw hole can be configured to allow for more than one angle of insertion for a screw. In some cases, additional features can be realized by selecting the shape of the screw hole. That is, the screw holes in a dorsal plate can have a circular shape, or alternatively one or more non-circular shape can be included. In one example, at least one screw hole has an elongated shape. One such elongated shape is illustrated by the two distal screw holes in the plate shown in FIG. 1A. An elongated screw hole can also allow a greater degree of freedom for selecting a point on the bone for insertion of a screw. In another example, a non-circular hole shape (e.g. square or star-shaped) can be used for insertion of a screw having a similarly shaped head, which can serve to secure the screw in place once fully inserted.

Figure 1C:
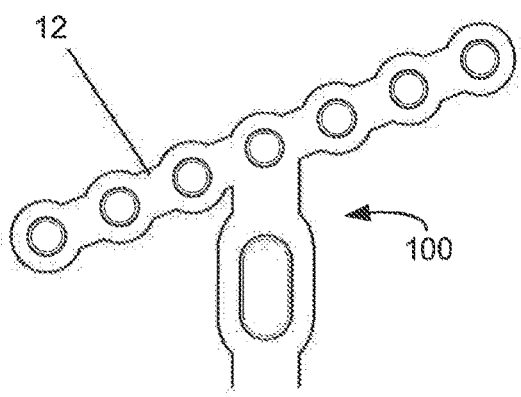
FIG. 1C is a top view diagram of the transverse portion of a dorsal plate according to still another example of the present disclosure.

The transverse portion 12 can further be shaped or otherwise configured for effective attachment to the distal extremity of the radius. The dorsal plates in FIGS. 1A through 1C show examples of shapes that can be exhibited by transverse portions in accordance with the present disclosure. The transverse portion can be substantially linear within the x-y plane as illustrated in FIG. 1C, or alternatively, the transverse portion can have a curvature in that plane, as shown in FIGS. 1A and 1B. In a particular example, this curvature can approximate a distal/proximal curvature exhibited by the dorsal articular surface. In both straight and curved transverse portion examples, at least a part of the transverse portion is situated at an angle from perpendicular to the longitudinal portion 10, as described above. As shown in the diagram of FIG. 1A, in one aspect, each transverse portion has a radial branch 18 that forms an obtuse angle 20 with the longitudinal portion. In another aspect, the transverse portion has an ulnar branch 22 that forms an acute angle 24 with the longitudinal portion. In an aspect of these examples, the degree of angle and/or curvature of either or both branches can be selected to allow the transverse portion to be positioned for solid attachment to bone.

Figure 3:
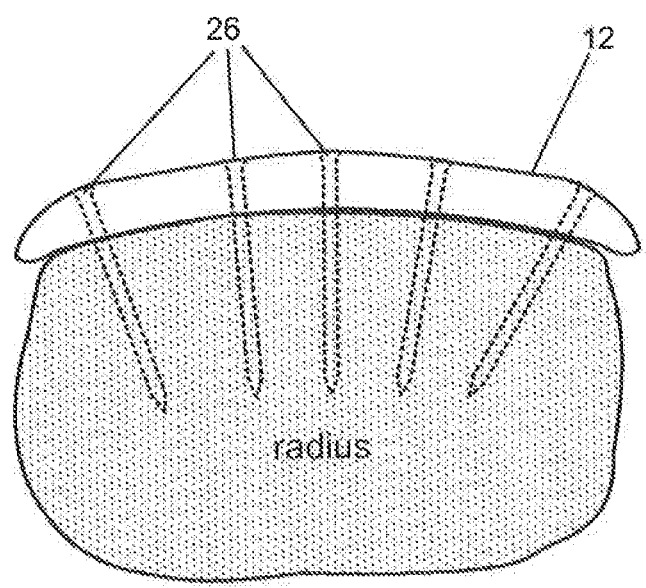
FIG. 3 is a cross-section diagram of a distal radius to which is attached a transverse portion of a dorsal plate according to an example of the present disclosure.

FIG. 3 shows a cross-section of a distal radius with the transverse portion 12 of a dorsal plate attached thereto. As shown, the transverse portion 12 can also have a z-axis curvature (e.g., in the dorsal/volar axis with respect to the distal radius). In a particular example, the curvature can correspond to a dorsal/volar curvature of the articular surface of the distal radius. Curvature of the transverse portion in this axis can allow the transverse portion to be closely associated with the surface of the radius along substantially the whole length of the transverse portion. This in turn allows attachment screws 26 to be inserted into the surface of the bone at or near a normal angle.

In one example, the transverse portion can be configured to be bendable so as to provide a particular curvature. In some cases, this may be facilitated by having the plate partially installed so that the transverse portion can be matched to the curvature of the subject's radius. Accordingly, in a particular example, the transverse portion is configured to be bendable or malleable after part of the plate (e.g. the longitudinal portion) has already been attached. This flexibility is exhibited along substantially the entire length of the transverse portion (rather than being restricted to specific regions), allowing more complete correspondence between the curvature of the transverse portion and the contour of the distal radius. In a particular aspect, the flexibility allows independent positioning of each screw hole relative to the radius surface. The bendability of the transverse portion can be a product of the materials chosen for the plate as well as the thickness of the transverse portion. In another example, the attachment point between the transverse portion and the longitudinal portion is configured so that the angle is adjustable.

As noted above, a method of fixing a wrist fracture using a dorsal approach can comprise dissecting and retracting a flap of the retinaculum prior to attachment of the dorsal plate to the radius. The extensors and other underlying tissue can also be retracted to expose the bone for attachment of the plate. Once the plate has been attached, the flap of retinaculum can be drawn over the plate so as to cover the transverse portion. With the flap in place, the tendons can be released to resume their original orientation, where the flap is now interposed between the tendons and the plate. In accordance with the example, the flap covers the transverse portion and prevents direct contact between the transverse portion and the overlying tendons. In this way the tendons are protected from friction from the dorsal plate, thereby reducing rupture or other complications that can arise from such contact. This approach is facilitated by the narrow profile of the transverse portion, so that the transverse portion can be partially or completely covered by the flap of retinaculum. In a further aspect, the size of the flap dissected from the original retinaculum can be minimized, reducing the postoperative impact of the procedure on retinacular function. In a particular example, a flap of about 1 cm in width can sufficient to completely cover the transverse portion, though more or less may be used at the discretion of the surgeon.

While the forgoing examples are illustrative of the principles of the present technology in one or more particular applications, it will be apparent to those of ordinary skill in the art that numerous modifications in form, usage and details of implementation can be made without the exercise of inventive faculty, and without departing from the principles and concepts of this technology. Accordingly, it is not intended that the technology be limited, except as by the claims set forth below.

The invention claimed is:

1. A method for fixation of a distal radial fracture, comprising:
　　dissecting a retinaculum of a wrist exhibiting a fractured distal radius to create a flap;
　　retracting the flap;
　　retracting tendons overlying the fractured distal radius;
　　attaching a dorsal plate to a distal extremity of the fractured distal radius,
　　wherein the dorsal plate comprises:
　　　　a single longitudinal portion having a distal end;
　　　　a transverse portion fixed across the distal end at a fixed angle of 18° to 26° from perpendicular with respect to the single longitudinal portion such that a radial branch of the transverse portion forms an obtuse angle with the single longitudinal portion and an ulnar branch of the transverse portion forms an acute angle with the single longitudinal portion, wherein the transverse portion includes an x-y curvature, the transverse portion also having a convex z-axis curvature or being flexible to form a convex z-axis curvature, wherein said z-axis curvature corresponds to a dorsal contour of the distal extremity of the fractured distal radius;
　　　　a first plurality of screw holes positioned along the single longitudinal portion; and
　　　　a second plurality of screw holes positioned along the transverse portion, wherein there are at least two screw holes on each opposing side of the transverse portion; and
　　securing the flap to cover the transverse portion of the dorsal plate, wherein the transverse portion is at least partially covered by the flap of the retinaculum so that there is substantially no direct contact between the tendons and the transverse portion of the dorsal plate.

2. The method as recited in claim 1, wherein the method for fixation utilizes a dorsal approach for repairing the fractured distal radius.

3. The method as recited in claim 1, wherein the flap has a width of no greater than 1 cm.

4. The method as recited in claim 3, wherein the transverse portion of the dorsal plate has a width that is less than 1 cm.

5. The method as recited in claim 1, wherein at least a portion of the x-y curvature extends away from the single longitudinal portion.

6. The method as recited in claim 1, comprising: after securing the flap, releasing the tendons to resume their pre-retracted orientation.

7. The method as recited in claim 1, wherein the flap is interposed directly between the tendons and the transverse portion of the dorsal plate.

8. The method as recited in claim 1, wherein the tendons include extensors and other underlying tissue of the retinaculum.

9. The method as recited in claim 1, wherein the single longitudinal portion includes a flat cross-sectional profile.

10. The method as recited in claim 1, wherein the first plurality of screw holes consists of five screw holes.

11. The method as recited in claim 10, wherein at least two of the five screw holes are elongated in shape.

12. The method as recited in claim 11, wherein the at least two of the five screw holes that are elongated in shape are distal-most screw holes of the single longitudinal portion.

13. The method as recited in claim 1, wherein the second plurality of screw holes consists of seven screw holes.

14. The method as recited in claim 1, wherein there are at least three screw holes on each opposing side of the transverse portion of the dorsal plate.

15. The method as recited in claim 1, wherein the transverse portion of the dorsal plate has a width that is less than 1 cm and the single longitudinal portion of the dorsal plate has a width that is less than 1.25 cm.

16. The method as recited in claim 1, wherein the first plurality of screw holes are aligned along the single longitudinal portion and the second plurality of screw holes are not all aligned along the transverse portion of the dorsal plate.

17. The method as recited in claim 1, wherein the dorsal plate is made of iron, chromium, cobalt, molybdenum, nickel, or alloys thereof.

18. The method as recited in claim 1, wherein securing the flap comprises completely covering the transverse portion of the dorsal plate.

19. The method as recited in claim 1, wherein attaching the dorsal plate includes positioning the single longitudinal portion of the dorsal plate between an extensor pollicis longus (EPL) and an extensor carpus radialis *brevis* (ECRB) of the tendons.

* * * * *